United States Patent [19]
Asano et al.

[11] Patent Number: 5,704,368
[45] Date of Patent: Jan. 6, 1998

[54] METHOD OF, AND APPARATUS FOR, MEASURING ELECTROGASTROGRAM AND INTESTINAL ELECTROGRAM

[75] Inventors: Fumitaka Asano, Saitama; Yoshio Yamada, Tokyo, both of Japan

[73] Assignees: Gram Corporation, Shizuoka; Nissho Corporation, Osaka, both of Japan

[21] Appl. No.: 489,367

[22] Filed: Jun. 12, 1995

[30] Foreign Application Priority Data

Jun. 17, 1994 [JP] Japan .................................. 6-159488

[51] Int. Cl.$^6$ ................................................ A61B 5/04
[52] U.S. Cl. ................................... 128/733; 128/741
[58] Field of Search ............................. 128/733, 741

[56] References Cited

PUBLICATIONS

The Influence of Body Size to the Parameters of Gastric Slow Wave: Studied with and Assembled Electrogastrography, F-Y Chang, et al., Chinese Journal of Physiology 37(4): 219–223, Dec. 31, 1994.

Non-Invasive Electrogastrography, Parts 1 & 2, Archives of Physiology and Biochemistry, vol. 103, No. 4, pp. 436–441, Oct. 1, 1995.

*Primary Examiner*—Vincent Millin
*Assistant Examiner*—Robert N. Weiland
*Attorney, Agent, or Firm*—Browdy and Neimark

[57] ABSTRACT

An apparatus for measuring an electrogastrogram and an intestinal electrogram including at least an electrode fixed to a body surface, an amplifier for amplifying a potential detected by said electrode, a low-pass filter for removing frequency signals other than the potentials of the stomach and the bowel amplified by said amplifier and a recorder.

The relationship between the frequency of the input signal of said low-pass filter and the phase of the output signal is made linear.

7 Claims, 5 Drawing Sheets

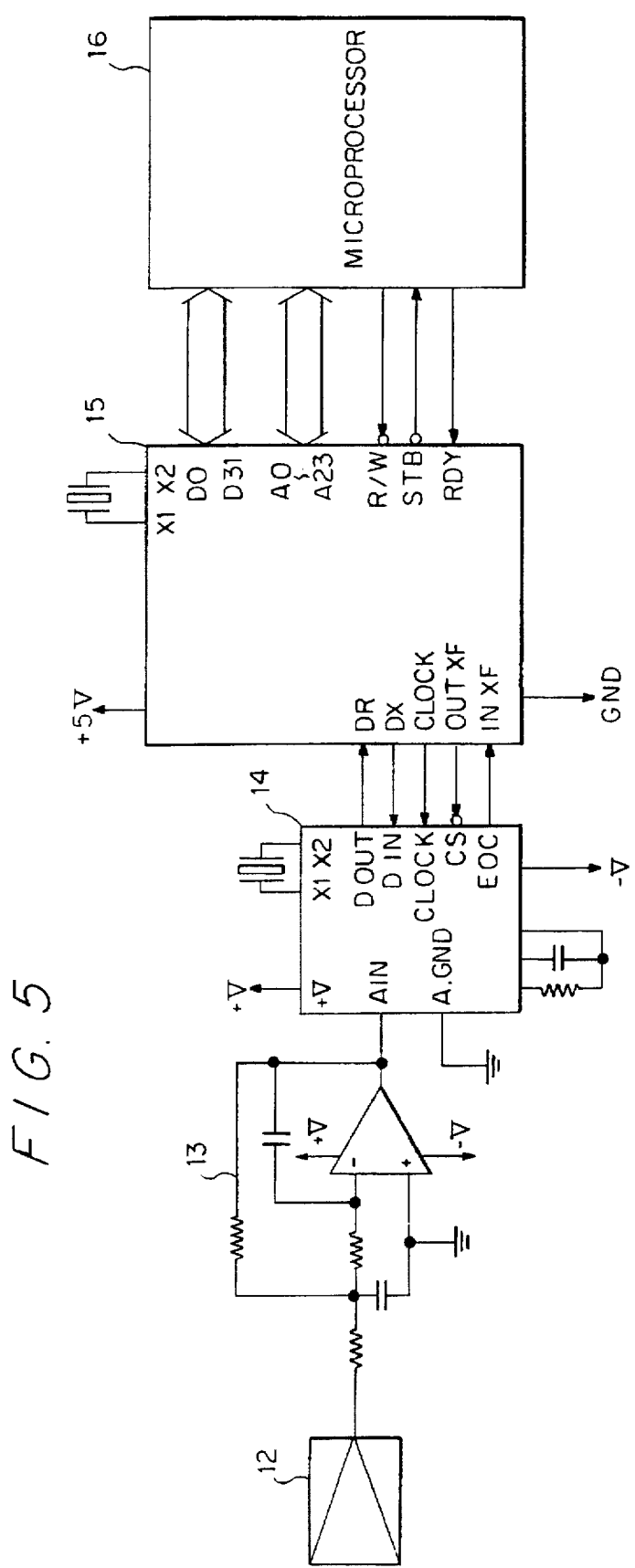
F I G. 5

METHOD OF, AND APPARATUS FOR, MEASURING ELECTROGASTROGRAM AND INTESTINAL ELECTROGRAM

BACKGROUND OF THE INVENTION

1. Field of the Invention

This invention relates to a method of, and an apparatus for, measuring a electrogastrogram and an intestinal electrogram for disposing mainly an electrode on the body surface of the human body, identifying the motion of the stomach and the bowel as potentials and recording the potentials so as to acquire information as guidelines for medication and remedy of various diseases.

2. Description of the Prior Art

To acquire the information described above, the motion of the stomach and the bowel must be observed. However, since it is difficult to measure the motion of the stomach and the bowel from the body surface, attempts have been made to measure the pressure inside the stomach by a catheter put into the body or to measure a myogenic potential of organs by a needle electrode. However, the information acquired by such measurements are far from being used as the guideline described above.

Various methods have been attempted to measure the motion of the stomach and the bowel from the potential of the electrode fitted to the body surface in order to acquire more accurate and detailed information which reflects the motion of the stomach and the bowel, but in this case, there is a critical problem that measurement cannot be made without being affected by respiration and body motion.

In other words, when measured by the electrode disposed on the body surface, the potential of the stomach and the bowel is as small as 20 to 200 μVpp and this potential is remarkably smaller than the potential obtained by an electrocardiogram. Further, the myogenic potential of the diaphragm with respiration strongly overlaps. Moreover, because the cycle of respiration (15 to 20 cycles/min) is approximate to the operation cycle (2 to 6 cycles/min) of the stomach and the bowel, a simple passive filter or an active filter having a low order according to the prior art cannot sufficiently remove the influences of respiration. Accordingly, measurement can be made for a short time for only those lean patients who are not easily affected by respiration, that is, those patients who have an extremely small subcutaneous fat layer which substantially serves as an insulator, while they are lying on their sides.

To evaluate clinically the stomach and the bowel, their daily activity must be known for a long time, and a body surface measurement method of the electrogastrogram and the intestinal electrogram can be said the sole means for satisfying this requirement.

Because the operation cycle of respiration is approximate to that of the stomach and the bowel as described above, a low-pass filter having steep cutoff characteristics is necessary to eliminate the influences of respiration. However, the filter having steep cutoff characteristics poses problems that phase characteristics are greatly distorted, over-shoot and ringing strongly appear, and distortion of the measured waveforms of the stomach and the bowel becomes great.

The potential of the stomach and the bowel is relatively smaller than other potentials. Therefore, if any fluctuation occurs in the level of the potential due to unstability of body motion and the electrode, the signals to be measured disappear, and when a filter having over-shoot is employed, a long time is necessary before returning to the original state. Such fluctuation of the potential frequently occurs during daily activity. Therefore, when a filter having over-shoot is used, measurement can be make only under the stationary state.

Ringing generates a false signal which is mistaken for the motion of the stomach and the bowel even due to small level fluctuation resulting from disturbance.

Distortion of the phase characteristics greatly changes the shape of measured waveforms, and makes it practically impossible to effect vector analysis which compares amplitude characteristics. A Bessel filter is known as a filter having small waveform distortion and devoid of over-shoot and ringing, but its cutoff characteristics cannot be improved even by increasing an order. Therefore, this filter is not practical. When an apparatus for adult, in which the cutoff characteristics of the filter for removing adjacent frequencies are fixed, is used for measuring children and newly born babies, measurement cannot be made because the motion of the stomach and the bowel is too fast and the necessary signals are removed by the filter.

SUMMARY OF THE INVENTION

As described above, it has been practically difficult in the past to measure the electrogastrogram and the intestinal electrogram for a long time without being affected by respiration. Therefore, the present invention aims at providing a method of, and apparatus for, measuring the electrogastrogram and the intestinal electrogram which makes it possible to carry out the measurement described above and can obtain the information as guidelines for the medication and remedy for various diseases.

Other and further objects, features and advantages of the invention will appear more fully from the following descriptions.

The present invention provides a method of and apparatus for measuring the electrogastrogram and the intestinal electrogram characterized in that a low-pass filter for removing high frequency signals other than the frequency signals contained in the potential of the stomach and the potential of the bowel is interposed between an amplifier for biological signals and a recorder for recording the signals amplified by the amplifier, and the relationship between the frequency of the input signal of the low-pass filter and the phase of the output signal is made linear. The present invention provides also an apparatus for measuring a electrogastrogram and an intestinal electrogram comprising at least an electrode fixed to a body surface, an amplifier for amplifying the potential detected by the electrode, a low-pass filter for removing frequency signals other than the potentials of the stomach and the bowel amplified by the amplifier and a recorder, wherein the relationship between the frequency of the input signal of the low-pass filter and the phase of the output signal is made linear. Preferably, the cut-off frequency of the low-pass filter is variable.

In the present invention, the order of the filter is increased so as to improve the cut-off characteristics of the low-pass filter for removing the influences of respiration, and moreover, the phase characteristics with respect to the frequencies of the input and output signals are made linear. Accordingly, over-shoot and ringing can be prevented, and distortion of the waveform can he reduced. Unless the low-pass filter used for the electrogastrogram and the intestinal electrogram is provided with the cut-off characteristics capable of removing the influences of respiration, is free from run-over of the phase characteristics and can make the phase change with respect to the frequency linear, practical measurement cannot be made.

Motions of the stomach and the bowel of children and newly born babies are faster than those of adult. However, motion of respiration is relatively faster, too, and measurement can be made under the optimum state in the same way as in the case of adult by allowing the cut-off frequency of the low-pass filter for removing the influences of respiration to change in accordance with the motions of the stomach and the bowel. Optimum filter characteristics are also different depending on the organs as the object of measurement (for example, the colon moves more quickly than the stomach), and it is most desirable that the cut-off frequency be variable.

BRIEF DESCRIPTION OF THE DRAWINGS

FIG. 5 is a more concrete circuit diagram of the block diagram shown in FIG. 2.

DESCRIPTION OF THE PREFERRED EMBODIMENTS

The present invention can be practised by two kinds of methods apparatuses.

Figure 3:
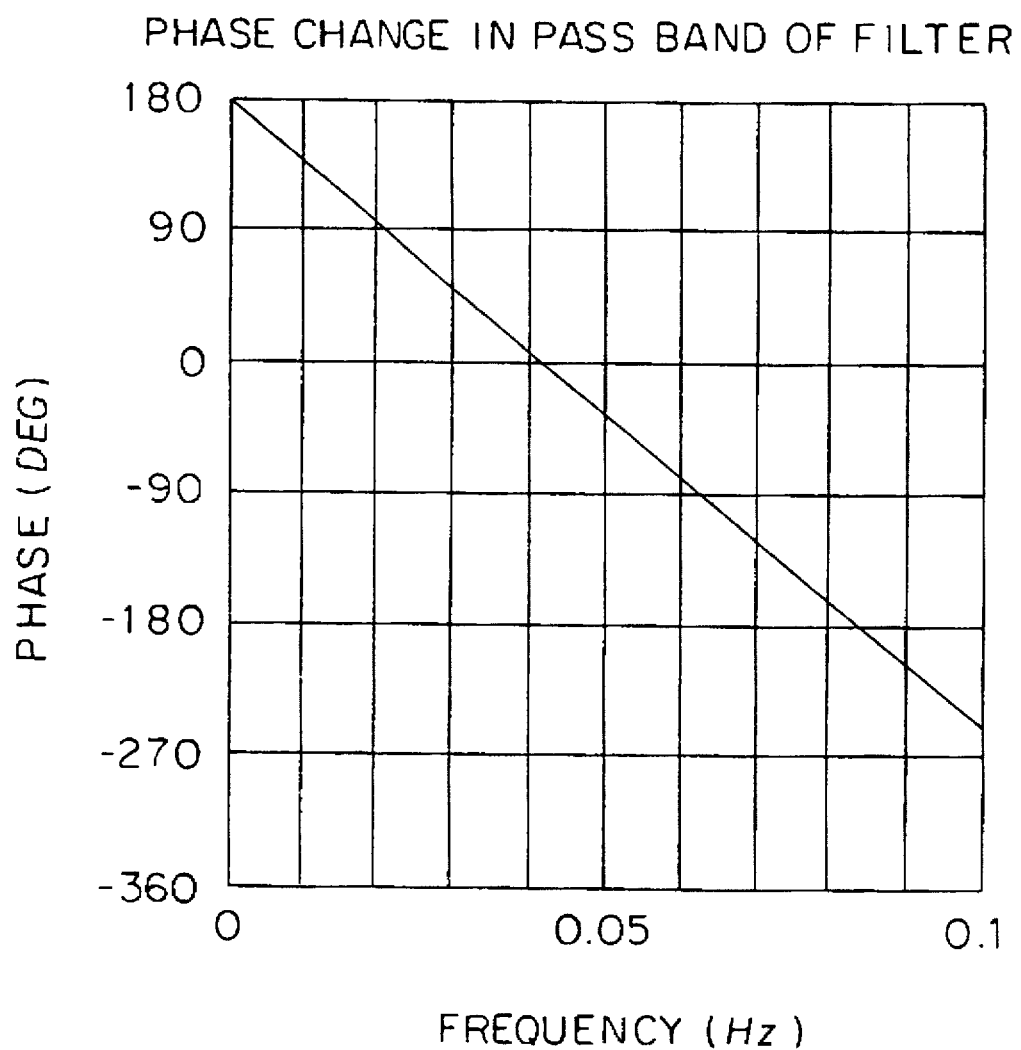
FIG. 3 is a graph showing the phase change in a pass band of a low-pass filter used in the present invention.

One of them constitutes a low-pass filter by which the phase relationship between the frequency of an input signal and that of an output signal is allowed to change linearly by analog signal processing. The low-pass filter can be constituted, for example, by using a switched capacitor LTC1164-7 of Linear Technology Co. (FIG. 3 is a graph showing the phase change in a pass band).

Another method or apparatus constitutes a digital signal obtained by converting an analog signal (A/D conversion) by using a digital filter so programmed as to provide the characteristics of the present invention. In the case of this method, filter processing is carried out after the analog signal is converted to the digital signal. The electrogastrogram and the intestinal electrogram can sufficiently evaluate the motion even by measurement of one channel, but multi-channel measurement is necessary to observe the motion of the stomach or to effect vector analysis.

First, an example of multi-channel measurement using the switched capacitor filter will be explained with reference to FIG. 1.

The electrogastrogram or the intestinal electrogram detected by an electrode 1 pasted to the body surface is amplified by an amplifier 2 to a level at which filter processing can be carried out. After high frequency components contained in the amplified signal are removed by a simple low-pass filter 3, the signal is applied to a switched capacitor 4. This capacitor 4 acts as a low-pass filter which provides the relationship between the frequency of the input signal and phase of the output signal with linear characteristics as required by the present invention.

Since the frequency of a given clock is proportional to a cut-off frequency, the switched capacitor filter 4 selects an optimum cut-off frequency by changing the frequency of a clock generator 8. The signal leaving the switched capacitor filter 4 is sent to an A/D convertor 6 by sequentially switching a plurality of channels by a signal switch 5. The A/D convertor 6 converts the analog signal to the digital signal and sends this digital signal to a recorder 7.

As many identical circuit components ranging from the electrode 1 to the switched capacitor filter 4 as the number of channels used are necessary. A block of another channel is denoted by reference numeral 9. Though various methods are known for constituting the signal switch 5 and the A/D convertor 6, this embodiment illustrates only a typical example. The recorder 7 ordinarily comprises a semiconductor memory, but a recording medium such as a magnetic tape and an optical disk may also be used.

The practical apparatus further requires a microprocessor for controlling the measurement cycle, the overall operations, display, and so forth, a control circuit of a power supply and a battery, a protective circuit for protecting the apparatus from static electricity, etc. but the explanation will be omitted because they are not directly relevant to the present invention.

Figure 1:
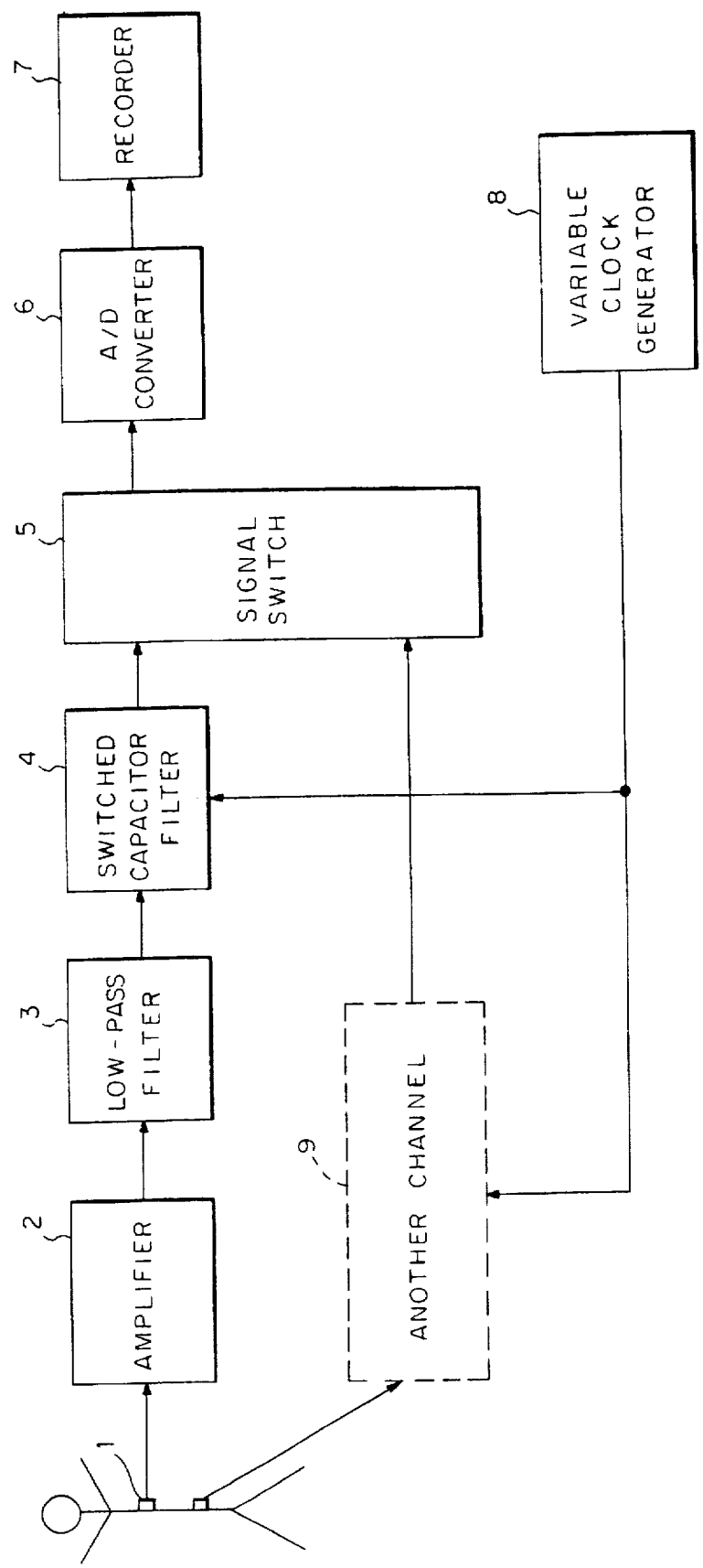
FIG. 1 is a block diagram showing principal portions when a low-pass filter satisfying the requirements of the present invention is constituted by using a switched capacitor filter and in a multi-channel construction.
Figure 4:
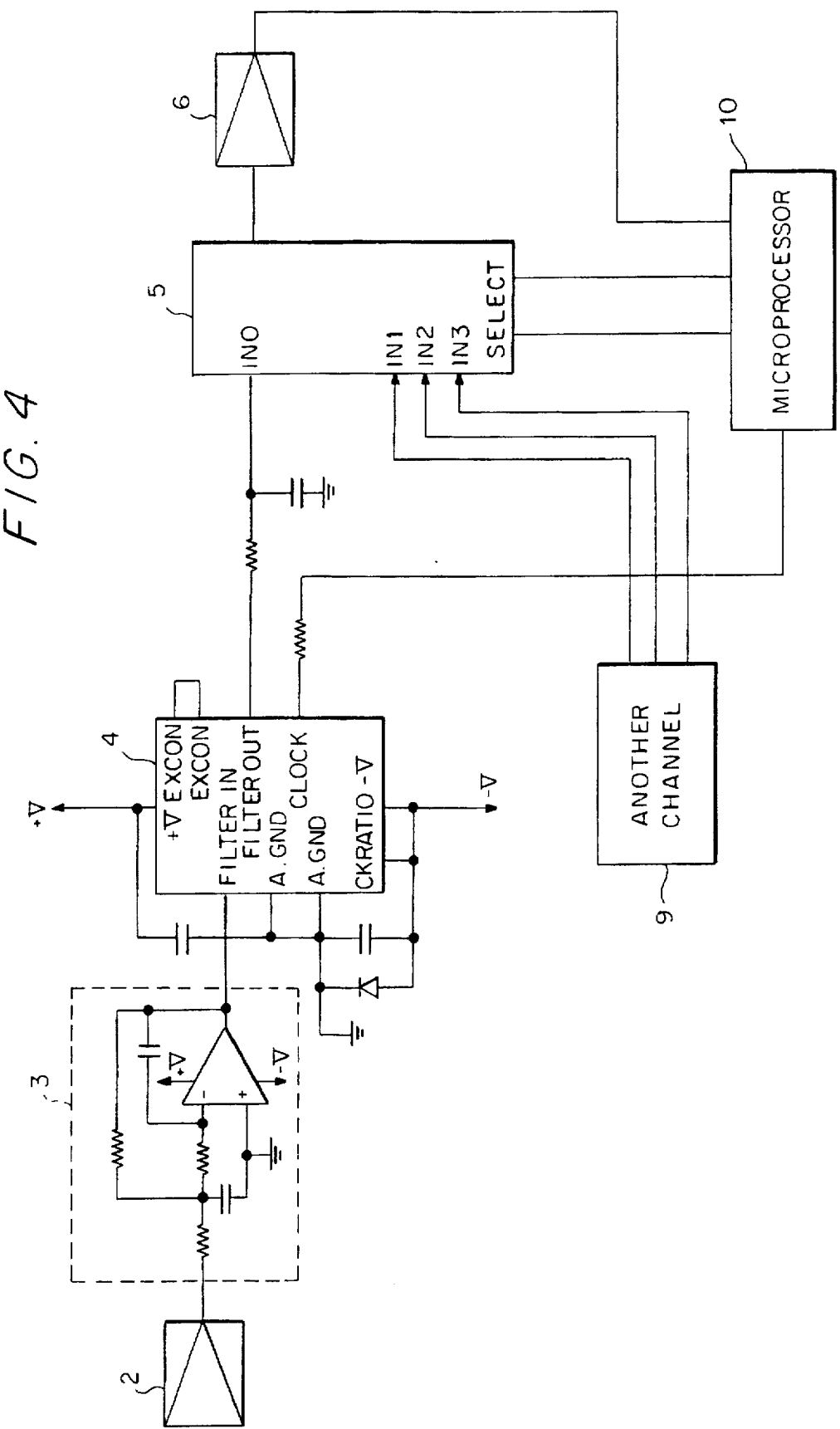
FIG. 4 is a more concrete circuit diagram of the block diagram shown in FIG. 1.

FIG. 4 is a circuit diagram showing more concretely the circuit members shown block-wise in FIG. 1, and like reference numerals are used to identify like circuit members as in FIG. 1. As shown in FIG. 4, the switch 5 is changed over by a control signal from the microprocessor 10. The clock of the switched capacitor filter 4 is supplied from the microprocessor 10. The cutoff frequency of this switched capacitor filter 4 can be changed by controlling the frequency of this clock.

Figure 2:
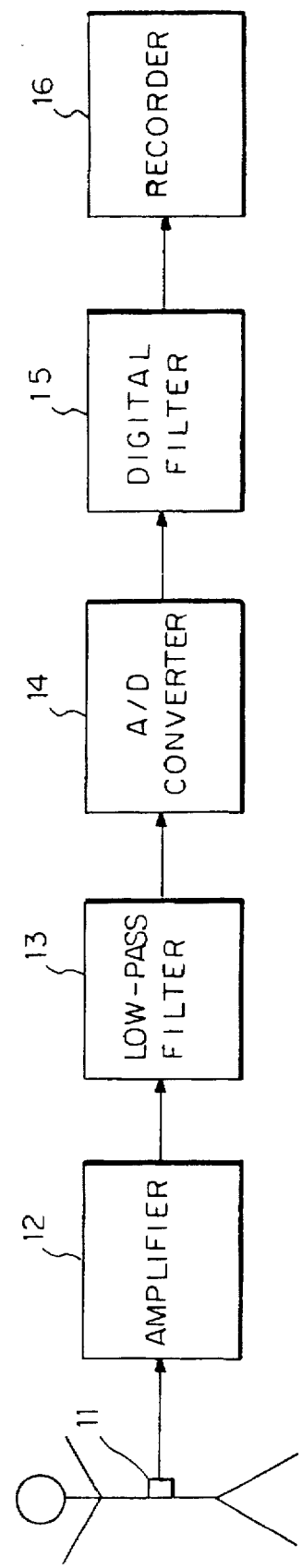
FIG. 2 is a block diagram of principal portions when the low-pass filter of the present invention is constituted by a digital filter and in one-channel construction.

Next, FIG. 2 shows an example of the one-channel construction using a digital filter. The electrode 11, the amplifier 12 and the low-pass filter 13 are the same as those in the construction using the switched capacitor filter described above. In this case, however, the low-pass filter 13 is employed so as to eliminate the high frequency components which would otherwise exert adverse influences on the A/D convertor 14 and the digital filter 15.

The A/D convertor 14 converts the analog signal to the digital signal and applies the digital signal to the digital filter 15. This digital filter 15 is programmed in such a manner as to constitute a low-pass filter providing the linear characteristics of the phase changes of the input signal and the output signal with respect to a frequency as the essential requirement of the present invention.

A dedicated semiconductor or DSP (Digital Signal Processor) is generally used for the digital filter 15, but the digital filter can be constituted by only a software if the microprocessor has high performance. Since the output of the digital filter 15 is the digital signal, the digital filter 15 can be directly connected to the recorder 16.

The method of changing the cutoff frequency by the digital filter 15 includes a method which changes the program constituting the filter and another which changes a period at which the signal is input to the digital filter after A/D conversion. From the aspect of the apparatus, the microprocessor for controlling the apparatus as a whole, the control circuit of the power supply and the battery, the protective circuits, etc, are necessary in the same way as in the case of the switched capacitor filter.

FIG. 5 is a circuit diagram showing more concretely the circuit members shown block-wise in FIG. 2, and like reference numerals are used in FIG. 5 to identify like members as in FIG. 2.

The low-pass filter 13 disposed on the input side of the A/D convertor 14 is a simple feedback type filter, and its output is supplied to the A/D convertor 14. The digital output of the A/D convertor 14 is supplied to the digital filter 15 which is controlled by the microprocessor 16. This digital filter 15 is referred to as a "digital signal processor (DSP)" and is used for various kinds of signal processing. A filter TMS320C30 of Texas Instruments Co. is an example of commercial products.

As described above, the present invention can measure the electrogastrogram and the intestinal electrogram for a long time without being affected by respiration. Because the practical activity of the stomach and the bowel during meal and sleep can be identified from outside the body, useful information for medication for various diseases and the guideline of remedy can be acquired. Therefore, the present invention greatly contributes to recovery of patients.

What is claimed is:

1. An apparatus for measuring an electrogastrogram and an intestinal electrogram comprising, active filter means for making a phase change with respect to a frequency linear, said filter means being able to remove frequency signals other than frequency signals contained in a potential of a bowel, said filter means being connected between an amplifier of biological signals and a recorder for recording the signals amplified by said amplifier;

whereas said apparatus can make the relationship between a frequency of an input signal of said filter means and a phase of an output signal of said filter is linear.

2. The apparatus of claim 1, wherein the filter means comprises a low-pass filter and a switched capacitor.

3. The apparatus of claim 2, wherein a cutoff frequency of said filter means is made variable.

4. The apparatus of claim 1, wherein a signal switch is connected to said filter means and an analog to digital convertor is connected between said signal switch and said recorder, said signal switch and said analog and digital convertor acting to convert an analog signal from said filter means to a digital signal sent to said recorder.

5. An apparatus for measuring an electrogram and an intestinal electrogram comprising, an electrode fixed to a body surface;

an amplifier connected to said electrode for amplifying a potential detected by said electrode;

active filter means connected to said amplifier for making a phase change with respect to a frequency linear, said filter means removing frequency signals other potentials of a stomach and a bowel amplified by said amplifier;

a recorder connected to said filter means;

wherein said apparatus can make the relationship between a frequency of an input signal of said filter means and the phase of an output signal linear.

6. The apparatus of claim 5, wherein the filter means comprises a low-pass filter, an analog to digital converter and a digital filter.

7. The apparatus of claim 6, wherein a cutoff frequency of said filter means is made variable.

* * * * *